United States Patent [19]

Ranby et al.

[11] Patent Number: 5,169,756
[45] Date of Patent: Dec. 8, 1992

[54] SOLID PHASE ANALYSIS METHOD

[75] Inventors: Gustaf M. Rånby, Umea; Nils A. Bergsdorf, Hornefors, both of Sweden

[73] Assignee: Biopool International, Inc., Ventura, Calif.

[21] Appl. No.: 38,740

[22] Filed: Apr. 15, 1987

[30] Foreign Application Priority Data

Apr. 15, 1986 [SE] Sweden ............................. 8601695

[51] Int. Cl.$^5$ .................. G01N 33/53; G01N 33/543; G01N 33/573
[52] U.S. Cl. ..................................... 435/7.4; 435/7.1; 435/7.9; 435/7.92; 435/7.93; 435/5; 435/15; 436/518; 436/528; 436/529; 436/534; 436/810; 436/815; 436/825; 436/531
[58] Field of Search ............... 436/518, 528, 529, 531, 436/534, 548, 809, 810, 811, 813, 815, 825; 435/7, 15, 7.1, 7.9, 7.94, 7.92, 7.4

[56] References Cited

U.S. PATENT DOCUMENTS 4,569,919 1/1986 Toth et al. .
4,661,445 4/1987 Saxinger et al. .

OTHER PUBLICATIONS

Boscato, L. M. et al., Clin. Chem., 32 (8), 1491–1495 (1986, Jul.).
Clark, P. M. et al., Clin. Chem., 31 (10), 1762 (letter) 1985.
Howanitz, P. J. et al., Clin. Chem., 28 (3), 427–431 (1982).
Rijken, D. et al., Journ. Lab Clin. Med., 101, No. 2: 274–284 (1983).
Holvoet, P. et al., Biol. Abstr. 81 (8): Abstract No. 69315, (1986).
Malvano, R., "Immunoenzymatic Assay Techniques", Martinus Nijhoff publishers, The Hague/Boston/London, pp. 104–115, 1980.
Maggio, E., "Enzyme-Immunoassay", CRC Press, Inc., Boca Raton, Florida, pp. 175–176, 1980.

Primary Examiner—Esther L. Kepplinger
Assistant Examiner—Toni R. Scheiner
Attorney, Agent, or Firm—Jones, Askew & Lunsford

[57] ABSTRACT

A method for the quantification or qualification of antigens with an immunological solid phase method, for example of the ELISA type, during which the invention seeks to overcome the difficulties with falsely high or falsely positive measurement results. This purpose is achieved by exposing two aliquots, preferably of the same size, of the sample containing the antigen that is to be determined to two solid phases with identical anti-antigen-antibody-coated surfaces, in which one exposure (exposure 1) occurs in the presence of antibodies present in the aliquot with the same specificity as the antibodies with which the solid phases are coated, and the other exposure (exposure 2) preferably occurs in the presence of antibodies present in the aliquot with non-specificity for the antigen in question, but otherwise essentially the same as the antibodies present in the aliquot in exposure 1, and the antigen is quantified by means of the difference between the bonded antigen in exposure 1 and the bonded antigen in exposure 2. The method is also applicable for detecting antibodies.

14 Claims, 1 Drawing Sheet

SOLID PHASE ANALYSIS METHOD

TECHNICAL FIELD

The present invention relates to the field of solid phase analysis for the detection of antigens with immunological solid phase methods.

BACKGROUND OF THE INVENTION

When an immunological solid phase method is used to measure or assay a certain antigen, a solid phase can be coated with antibodies against this antigen. This often occurs by physical adsorption of the antibodies on the inside of plastic tubes or wells in plastic plates ("coat" in the technical literature). When the antigen-containing test solution is placed in the tubes or wells, the antigen are selectively bonded (antibody-antigen reaction) to the adsorbed antibody. The tube or well can then be emptied and thoroughly washed. In this way antibody present on the surface can be transferred from the matrix (medium) in which it has been present, to a much more easily handled solid phase, where detection and quantification can be performed. With the well-known ELISA method, this is carried out with an additional antibody directed against the antigen. This antibody can be labelled with an enzyme such as horseradish peroxidase (HRP) or alkaline phosphatase. The enzyme-labelled (enzyme-conjugated) antibody is placed in the tube or well and is bonded to the antigen present on the walls or surfaces. The excess enzyme-labelled antibody is washed away, and the remaining enzyme-labelled antibody is detected with an enzyme substrate that is converted to a colored product.

The variations of the above-mentioned ELISA technique are numerous, but the fundamentals are the same. In theory only the antigen is removed from its original matrix to a surface where it is uniformly exposed and is accessible to analysis.

In practice, there are always other components in the test solution that are bonded to this surface, either to the absorbed antibody or directly to the solid phase by some other mechanism. These non-specifically bonded components represent a significant source of error in the method, since they can interfere with the analysis to be performed and give rise to falsely positive or falsely high measurement results. In the traditional ELISA technique, non-antigen components in the sample which are bonded to the solid phase can absorb enzyme-conjugated antibody and give a falsely high measurement result. These non-antigen-mediated measurement results are believed to result from nonspecific absorption.

In qualitative analysis (e.g., testing only for the presence or absence of antibodies or antigens in a sample) elevated assay responses due to nonspecific effects will cause a false positive result. Attempts to reduce the false positive effects by elevating the discrimination level of the assay will cause increases in the numbers of false negative results. Thus, nonspecific effects in these assays create uncertainty in the diagnosis.

Previous techniques have attempted to reduce non-specific absorption (or bonding) to a minimum. For example, the surface of the solid phase has been thoroughly "blocked" to make it incapable of absorbing additional components. In addition, the trapped antibodies have been enzymatically split and the antigen-bonding fraction ((Fab)$_2$- fragment) has been isolated and immobilized on the solid phase. However, total success has not been achieved with these techniques. Moreover, it should be noted that difficulties in using the ELISA technique have recently been noted to an increasing extent; see, for example, Gaffney et al., 1984, Thromb. Haemostas, 52 (1):96–97, Boscato, et al., 1986, Clin. Chem., 32 (8): 1491–1495

SUMMARY OF THE INVENTION

In accordance with the present invention, an improved method of detecting an antigen in a sample is provided comprising the steps of coating a first solid phase and a second solid phase with an antigen-specific antibody. The first solid phase is then exposed to a solution containing the same antigen-specific antibody used to coat the first and second solid phases and the antigen. The second solid phase is exposed to a solution containing a non-specific antibody and the antigen. The amount of antigen bound to the first solid phase and to the second solid phase is then determined by means well known to those of ordinary skill in the art. To quantify the amount of antigen in the sample, the amount of antigen bound to the first solid phase is subtracted from the amount of antigen bound to the second solid phase.

In accordance with a second embodiment of the present invention where one wishes to measure a particular antigen-specific antibody in a sample, the invention comprises coating a first solid phase and a second solid phase with an antigen that is specific for the antibody to be tested. The first solid phase is then exposed to a solution containing the same antigen used to coat the first and second solid phases and the antigen-specific antibody. The second solid phase is exposed to a solution containing a non-specific antigen and the antigen-specific antibody. The amount of antibody bound to the first solid phase and to the second solid phase is then determined by means well known to those of ordinary skill in the art. To quantify the amount of antibody in the sample, the amount of antibody bound to the first solid phase is subtracted from the amount of antigen bound to the second solid phase.

The present invention relates to a method wherein one exposes the sample to be analyzed or assayed, with respect to antigen, to a solid phase coated with antibodies against the antigen in order to cause antigen-antibody bonding, whereupon one then detects or measures the bonded antigen by methods well known to those of ordinary skill in the art.

The novelty of the invention is based on the unexpected discovery that, by performing this exposure in the presence of certain special antibodies soluble in the sample, one eliminates or reduces the problem of non-specific adsorption. In an attempt to solve the problem of nonspecific adsorption of conjugate when developing ELISA for the enzyme tissue plasminogen activator (t-PA), we investigated the effect of soluble antibodies in the first incubation step, i.e., when the tested sample is exposed to a solid phase coated with antibody. We then made two important observations, namely:

1. Even relatively low concentrations of anti-t-PA-antibodies, having the same specificity as that used to coat the surface of the solid phase, was sufficient to block the specific t-Pa result. The expected result would have been that specific antibodies in the liquid phase (sample phase) would result in a distribution of t-PA-antigen between the two phases in accordance with the relative amounts of antibodies in the two phases. For example, if 0.2 µg of antibody were associated with the solid phase and 2 μg with the liquid phase, the antigen should be distributed 1 to 10 between the solid and liquid phases respectively. In practice, the distribution is 1 to 99 in such cases. This discovery permits a method where the soluble antibody is first placed in the measurement well (or tube) and the sample is then added to the same tube, which from a practical standpoint, is a highly attractive method. The need to preincubate the sample with dissolved antibody would make the method more difficult.

2. When antibodies from nonimmunized animals (so-called normal antibodies) are included in the first incubation, the result is generally reduced when the tissue plasminogen activator (t-PA) in the blood plasma was determined with the ELISA technique. In some cases, the reduction was greater than 50%, but usually approximately 10%. Only in one case out of 45 was such a reduction undetected. In advance, a reduction could only be expected in rare cases, namely in samples containing so-called rheumatoid factors. (No effect of protein as such was expected, because the 10 μg/ml of normal antibodies that were added were completely overshadowed by the 3000 μg/ml of protein that came from the blood plasma sample.)

The present invention is especially applicable to a noncompetitive immunological solid phase method such as the ELISA technique; see Engvall, 1980, *Methods enzymol.* 70A, 419–439. The invention represents a practical, useful solution to the problem of non-specific adsorption and has been shown to substantially improve the possibilities for reliable measurement or analysis results in certain analysis methods.

Accordingly, it is an object of the present invention to provide an improved assay wherein the number of false positives values is greatly reduced or eliminated.

It is a further object of the present invention to provide an improved assay wherein the number of falsely high values is greatly reduced or eliminated.

Yet another object of the present invention is to provide an improved assay wherein one can accurately measure the amount of antigen-specific antibody in a sample.

Another object of the present invention is to provide an assay wherein one can accurately measure the amount of antibody specific for the AIDS virus and reduce the number of false positives.

Another object of the present invention is to provide an assay wherein one can accurately measure the amount of tissue plasminogen activator in a sample.

Another object of the present invention is to provide a qualitative assay wherein the number of false positives are reduced to a minimum.

These and other objects, features and advantages of the present invention will become apparent after a review of the following detailed description of the disclosed embodiment and the appended claims.

DETAILED DESCRIPTION

Figure 1:
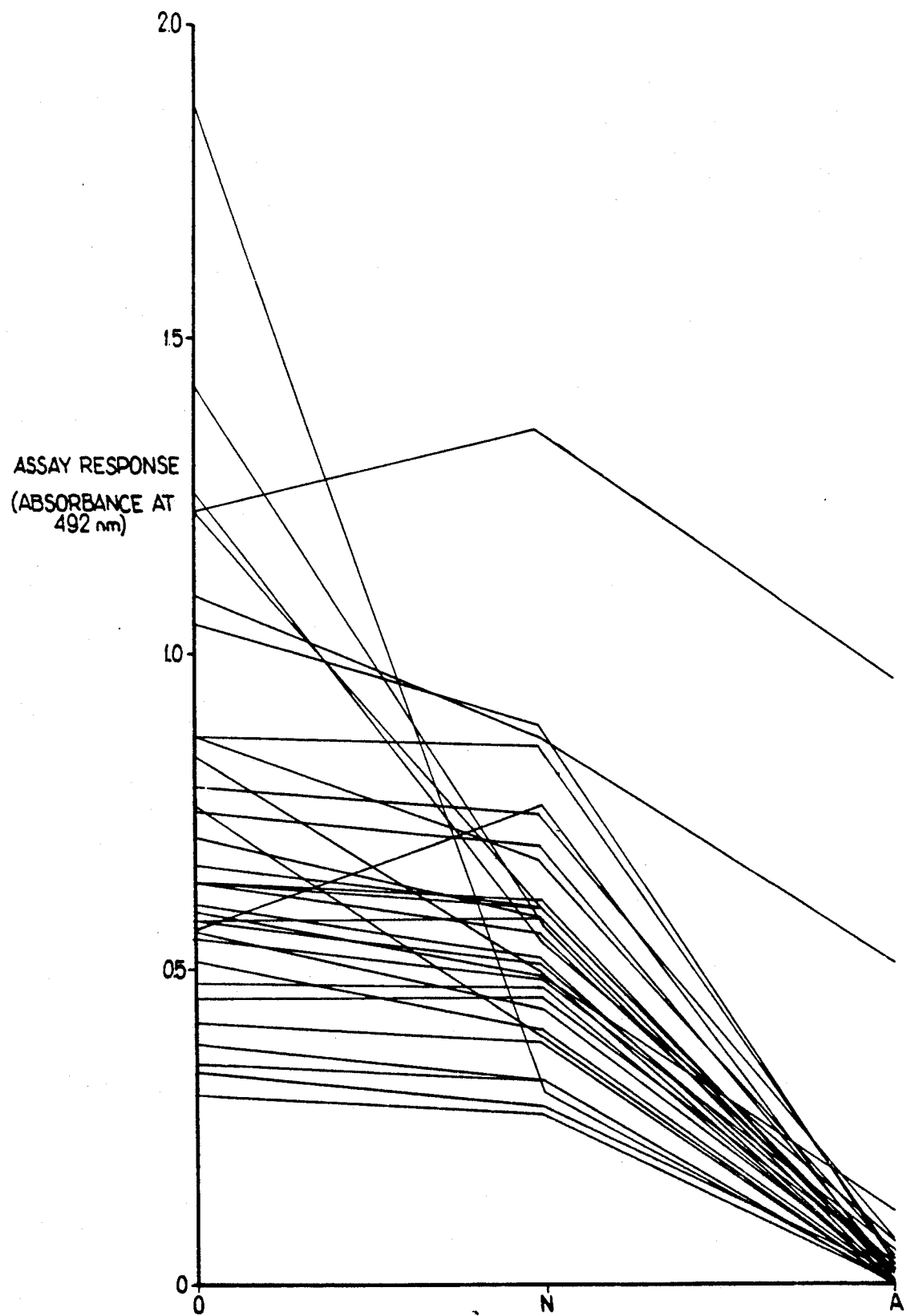
FIG. 1 is a comparison of measurement results during determination of t-PA with the ELISA method in 43 blood plasma samples. For each sample, the measurement was made in three measurement wells with prefilling of 150 μL PBS-Tween (O), 150 μL 10 mg/l normal IgG (N) and 150 μL 10 mg/ml anti-t-PA IgG (A) during the sample incubation step. The results of the same sample are connected with a line.

The total ELISA response, $R_{tot}$, can be viewed as composed of three parts: (a) an antigen-specific part, $R_{Ag}$, that can be quenched by adding antigen-specific immunoglobulins to the sample; (b) an antigen-unspecific part that can be quenched by adding nonimmune immunoglobulins to the sample, and hence should be termed immunoglobulin-specific response, $R_{Ig}$; and (c) an unspecific residual part, $R_{Ur}$, which is unaffected by and unrelated to the presence of immunoglobulins. Thus:

$$R_{tot} = R_{Ag} + R_{Ig} + R_{Ur}.$$

When the sample is added to micro-test plate wells containing antigen-specific antibodies ("prefill A" wells), both the $R_{Ag}$ and the $R_{Ig}$ are eliminated from the response, which here is called $R_A$, thus: $R_A = R_{Ur}$. When the sample is assayed in wells containing antibodies from non-immunized animals ("prefill N" wells), only $R_{Ig}$ is eliminated from the response, which is here called $R_N$: $R_N = R_{Ag} + R_{Ur}$. The difference between $R_N$ and $R_A$ is therefore the antigen-specific part of the assay response, i.e., the goal of the assay procedure: $R_N - R_A = R_{Ag}$. The possibility for false-positive results is inherent to ELISA techniques as currently practiced. With the method according to the present invention, it is become possible to essentially eliminate non-specific adsorption in a simple way.

The present invention differs from previous attempts to solve this problem in that we discovered a practical method for completely blocking specific bonding. The sample is incubated in two systems. In one, specific bonding is not selectively blocked and in the other it is. Non-specific bonding is expressed in both systems and the specific result is obtained as the difference.

In performing the present invention, three antibody preparations are used. A first one for coating the solid phase, a second one with the same specificity for blocking the specific measurement reading (this can be the same antibody preparation as used for the coat), and a third one which does not block the specific result. The latter two antibody preparations represent a pair and should be as similar as possible to each other. They preferably should only differ in one property, namely the reaction with antigen. One should react (be specific) and the other should not react (be nonspecific) with the antigen. The antibodies should therefore have the same or similar origin (for example, be derived from the same animal species, both being monoclonal of the same subgroup or both being polyclonal) and should be prepared in the same or a similar way.

In accordance with the present invention, to overcome the difficulties connected with falsely high or falsely positive measurement results, one exposes two aliquots of the sample containing the antigen to be determined to two solid phases with identical anti-antigen-antibody-coated surfaces. One exposure (exposure 1) is performed in the presence of antibodies in the sample having the same specificity as the antibodies with which the solid phases are coated, and the second exposure (exposure 2) preferably being performed in the presence of antibodies in the sample having non-specificity for the antigen in question, but otherwise essentially the same as the antibodies present in the sample in exposure 1, and one detects the antigen by means of the difference in the assay response between the bonded antigen in exposure 1 and the bonded antigen in exposure 2.

The method according to the present invention is primarily intended for use in a non-competitive immunological solid phase method of the ELISA type, which also means that the antibody referred to should preferably be immunoglobulin. The method is, of course, primarily intended for quantitative determination of antigen, but the method according to the invention is also suitable for qualitative analysis, where the uncertainty in the assay might be so great that the qualitative result could be questioned. In other words, the term "detects" in the present invention means both a determination of the quantity of an antigen and the presence of an antigen. It is to be understood that the term "quantify" as used herein refers to both quantitative measurement and qualitative measurement of an antigen or antibody in a sample.

As should be clear to a person of ordinary skill in the art, the two aliquots of the sample exposed in exposures 1 and 2 are preferably the same, because in this way one directly obtains the desired difference between bonded antigen in exposure 1 and bonded antigen in exposure 2 without any additional sources of error. However, this does not rule out performance of the method with different aliquots, i.e., test amounts or quantities of the sample, provided that one knows the quantities of the aliquots precisely. It should also be noted that the antigen sample to be tested can be added simultaneously with the specific and non-specific antibody to the two solid phases or the antigen sample can be added to the two wells after the specific and non-specific antibodies have been added.

For the analysis according to the invention to be optimally reliable, exposure to the two solid phases should be performed under virtually identical conditions. This means that both solid phases are essentially identical to each other, but it is theoretically sufficient that the solid phases are provided with essentially identical anti-antigen-antibody-coated surfaces.

The expression "antibodies dissolved in the sample" or similar expressions preferably mean that the antibodies added or present in the sample during the actual sample exposure are essentially soluble in the test substance being analyzed. However, this does not exclude the possibility that these are also immobilized on a solid phase, provided that the phase can be separated from the solid phase when detection of the antigen is accomplished.

As was mentioned above, the antibodies present in exposure 1 have the same specificity as the antibodies with which the solid phase has been coated. In principle, this means that the antibodies react with or bind to the antigen to be detected and block the ability of the antigen to react with antibody on the solid.

In contrast, the antibodies present in exposure 2 exhibit non-specificity for the antigen in question, i.e., they do not react with or bond to the antigen. Otherwise, however, they should be essentially identical to the antibodies present in exposure 1, which means that they are of the same origin (same animal species) and are prepared with essentially the same method. The expression "same", however, should be given a reasonable interpretation in this connection, because the inventive concept will not go lost if the antibodies are not "the same" in any way that is totally irrelevant to the invention.

In addition to the detection of the antigen by means of the difference between the bonded antigen during exposure 1 and the bonded antigen during exposure 2, this detection is performed according to a procedure known to persons of ordinary skill in the art. Thus, further description of the detection procedure will not be described herein.

The method of the present invention for detecting antigen is of special interest for the detection of the antigen t-PA (tissue plasminogen activator) in biological samples. Blood plasma, synovial fluid, cerebrospinal fluid, seminal fluid or cell culture media can be cited as examples of such biological samples.

An especially preferred embodiment of the method of the present invention involves placing the antibodies first on the device, for example, a test tube or a plate with wells, which comprises the solid phase, so that the soluble antibodies are already in place on the inner surface of the tube or wells when the actual sample is added. In this way the invention is utilized in a practical and economically advantageous manner while, at the same time, a reliable result is obtained.

It is to be understood that the solid phase referred to in the description of the present invention can also be particles such as beads. These composition of the particles includes, but is not limited to, agarose, polystyrene, latex, and polymethacrylate. The particles can be any shape.

In this especially preferred embodiment of the method of the present invention, one can first add a volume of the antibodies corresponding to 5-95% of the volume of the device in question. Preferably, the volume of the antibodies corresponds to 10-90% of the volume of the devise. More preferably, the volume of the antibodies corresponds to 20-80% of the volume of the devise.

As regards the amounts of the antibody present during exposure 1 or exposure 2 respectively, a suitable concentration interval has been shown to be between approximately 1 to 100 mg/l. However, the invention is in no way limited to this range. A preferable range is between 20 and 80 mg/l. It is to be understood that the range of antibody concentration is dependent upon the particular assay being performed. However, the range of between approximately 1 to 100 is especially suited for the above-mentioned determination of t-PA in biological samples.

Although the invention has been generally described and explained in connection with detection of an antigen, the method of the present invention should also be applicable for the directly opposite reaction, i.e. for the detection of antibodies. In other words, the detection of antibodies is also within the scope of the present invention.

More specifically, the method of the present invention relates to the detection of antibodies by an immunological solid phase method, wherein one exposes the sample to be determined with respect to antibodies to a solid phase coated with antigen specific for the antibody to produce an antibody-antigen bond, whereupon one determines the bonded antibody in a known manner.

To overcome falsely high or falsely positive results according to the present invention, one exposes two aliquots, preferably of the same size, of the sample containing the antibody to be determined to two solid phases with identical antigen-coated surfaces, one exposure (exposure 1) being performed in the presence of antigens dissolved in the aliquot having a specificity similar to that of the antigens with which the solid phases have been coated, and the other exposure (exposure 2) being performed in the presence of antigens dissolved in the aliquot having a non-specificity for the antibody in question. The antigens in exposure 2 should otherwise be similar in structure to the antigen dissolved in the aliquot in exposure 1. One detects the antibody by means of the difference between the bonded antibody in exposure 1 and the bonded antibody in exposure 2. This method can be used in detecting HTLV III-specific antibodies (HIV AIDS virus-specific) in body fluids. Other antigen-specific antibodies that can be measured by the present invention include, but are not limited to, cardiolipin, phosphatidyl choline, collagen, hepatitis A antigen, hepatitis B antigen, and Borelea.

Generally, the method of the present invention is performed according to the following procedure:

Microtiter plates are coated with antibody by incubating in the wells of the plates 100-1000 μl of a solution containing 1-100 mg/l antibody and 0.1-1.0 mol/l NaHCO$_3$ while shaking gently for two to four hours at 20°-30° C. Buffers that can be used in the coating process include, but are not limited to, protein non-denaturing buffer containing a protein nondenaturing detergent like Tween 20, Triton X-100, Pluronic surfactants, e.g., (phosphate buffered saline (PBS) Tween or PBS Tween with EDTA.

The wells are emptied and the contents washed with PBS Tween.

For each sample, two wells are filled, one with 100-200 μl of normal antibody, 5-15 mg/ml, and one with 100-200 μl of a specific antibody, 5-15 mg/ml, both dissolved in PBS Tween. Alternatively, the buffer can be PET buffer which contains EDTA. If the PET buffer is used, the acidification procedure described below is not necessary.

Blood samples are collected in the conventional manner and are centrifuged at 1000-3000×g for several minutes. The plasma is acidified by incubating approximately one volume of plasma with one volume of acidification buffer, such as sodium acetate buffer, pH 3.5-4.5, for 10-20 minutes at 20°-30° C. The acidified plasma is neutralized by adding one volume of pH-adjusting buffer, such as sodium phosphate-Tris, pH 8-11.

A 20 to 50 μl aliquot from each plasma sample is placed in wells pre-filled with normal or specific antibody, respectively, in a concentration of 5-15 mg/l dissolved in PBS Tween. The sample is incubated for 4-5 hours at 20°-30° C. while shaking carefully.

The wells are emptied of their contents and are washed with PBS Tween.

A 100-300 μl aliquot of HRP-conjugated antibody, 1-3 mg/l, dissolved in PBS Tween, is incubated for 4-5 hours at 20°-30° C. in the wells.

The wells are emptied of their contents and are washed with PBS Tween or PBS Tween with EDTA.

A 100-300 μl aliquot of peroxidase substrate dissolved in citrate-phosphate buffer, pH 4-6, is then incubated in the wells at 20°-30° C. in the dark for 20-40 minutes.

The substrate reaction is interrupted by adding 10-100 μl of 4-5 mol/l of H$_2$SO$_4$.

The absorbance at 490-495 nm is recorded. The difference in absorbance between the wells filled with normal antibody and the wells filled with specific antibody is calculated for the respective plasma samples. This represents the antigen-specific part of the response; this is compared with a standard curve wherein antigen is diluted in normal blood plasma.

The following specific examples will illustrate the invention as it applies in particular to measurement of tissue plasminogen activator It will be appreciated that other examples will be apparent to those of ordinary skill in the art and that the invention is not limited to these specific illustrative examples.

EXAMPLE 1

Below is a description of the protein components, less common chemicals and buffers used in the example.

Goat anti-t-PA IgG antiserum against t-PA from the human uterus is produced in the goat. The IgG fraction is purified by chromatography on A-Sepharose protein. The preparation is lyophilized and, when used, is reconstituted in water.

Normal goat IgG. The IgG fraction from the serum of a nonimmunized goat is purified by chromatography on A-Sepharose protein. The preparation is lyophilized and, when used, is reconstituted in water.

Horseradish peroxidase conjugated goat anti-t-PA IgG. The goat anti-t-PA IgG (described above) is conjugated to horseradish peroxidase (HRP Sigma Type VI) by the glutaraldehyde method. The conjugate is purified from free peroxidase by chromatography on A-Sepharose protein.

Tissue plasminogen activator (t-PA) in its single-chain form from human melanoma cells; lyophilized preparation with bovine serum albumin as carrier.

1, 2-Phenylenediamine (O.P.D.) peroxidase substrate, synthetic quality from Merck Chemical Co., Rahway, N.J.)

PBS-Tween buffer, 20 mMl/l sodium phosphate buffer, 100 mmol/l NaCl, 0.1 g/l Tween 20, pH 7.4.

PET Buffer, 20 mmol/l sodium phosphate buffer, 100 mmol/l NaCl, 10 mmol/l EDTA, 0.1 g/l Tween 20, pH 7.9.

Citrate-phosphate buffer, 100 mMl/l sodium dihydrogen phosphate is adjusted to pH 5.0 with 100 mMl/l citric acid.

Acidification buffer, 1.0 Ml/l sodium acetate buffer, pH 3.9.

pH adjusting buffer, 50 mMl/l sodium phosphate, 500 mMl/l Tris (Tris-hydroxymethylaminomethane), pH 10.4.

The ELISA methodology used in the example is based on the method of Bergsdorf et al., 1983, *Thromb. Haemostas.*, 50 (3), 740-744.

Determinations of the t-PA antigen concentrations in the plasma are carried out as follows:

Ninety-six-well microtest plates (Nunc immunoplate 1, Nunc, Denmark) are coated with anti t-PA IgG by incubating in the wells of the plates 200 μl of a solution containing 10 mg/l anti t-PA IgG and 0.1 mol/l NaHCO$_3$ while shaking carefully for three hours at 25° C.

The wells are emptied and the contents washed with PBS Tween or PET buffer.

For each sample, two wells are filled, one with 150 μl of normal IgG, 10 mg/ml, and one with 150 μl of anti-t-PA IgG, 10 mg/ml, both dissolved in PBS Tween.

Blood samples are collected in the conventional manner (sodium citrate or EDTA) and centrifuged within 5 minutes at 2000×g for five minutes. The plasma is acidified by incubating one volume of plasma with one volume of acidification buffer for 15 minutes at 25° C. The acidified plasma is neutralized by adding one volume of pH-adjusting buffer. If PET buffer is used in this procedure, the acidification of the plasma is not required.

A 20 to 50 μl aliquot (depending on the t-PA content in the sample; measurement result is independent of the added volume within this range) from each plasma sample is placed in wells pre-filled with normal or anti-t-PA IgG, respectively, in a concentration of 10 mg/l dissolved in PBS Tween. The sample is incubated for 3 hours at 25° C. while shaking carefully.

The wells are emptied of their contents and are washed with PBS Tween or PET buffer.

A 200 μl aliquot of HRP-conjugated t-PA IgG, 2 mg/l, dissolved in PBS Tween or PET buffer, is incubated for 3 hours at 25° C. in the wells.

The wells are emptied of their contents and are washed with PBS Tween.

A 200 μl aliquot of substrate (O.P.D./$H_2O_2$) dissolved in citrate-phosphate buffer, pH 5.0, is then incubated in the wells at 25° C. in the dark for 30 minutes.

The substrate reaction is interrupted by adding 50 μl of 4.5 Ml/l of $H_2SO_4$.

The absorbance at 492 nm is recorded. The difference in absorbance between the wells filled with normal IgG and the wells filled with anti-t-PA IgG is calculated for the respective plasma samples. This represents the t-PA-specific part of the response; this is compared with a standard curve wherein t-PA is diluted in normal human plasma.

EXAMPLE 2

The following experiment is run to investigate the requirement for a method to correct an incorrect result obtained because of nonspecific bonding effects, when the ELISA methodology is used to determine t-PA antigen concentrations.

Plasma samples from 34 patients are analyzed by ELISA. The samples are placed in wells filled with PBS Tween, normal IgG or anti-t-PA IgG.

The results are shown in FIG. 1. The samples placed in wells filled with normal IgG exhibit much lower absorbance than the samples placed in wells with PBS Tween. In 31% of the cases (13/34) the difference is greater than 100 milliabsorbance units. Individual samples exhibit high absorbance even in the presence of anti-t-PA IgG. Thus, it is necessary to use the methodology according to the present invention with both normal and anti-t-PA antibodies in order to avoid a falsely positive result due to nonspecific absorption during antigen concentration determinations by the ELISA technique (or similar techniques).

EXAMPLE 3

To further investigate the frequency of plasma samples that produce high nonspecific bonding, samples from 519 individuals are analyzed with respect to t-PA concentration. The plasma samples are placed in wells filled with anti-t-PA IgG as described above. These wells are designated "Prefill A Wells". The results are given in Table 1.

TABLE 1

Assay Response (A492) Measured in Prefill A Wells with 519 Plasma Samples Assayed for t-Pa Antigen by the Present Invention

| $A_{492}$ | n |
|---|---|
| <75 | 454 |
| 75-100 | 46 |
| 101-125 | 10 |
| 126-150 | 6 |

TABLE 1-continued

Assay Response (A492) Measured in Prefill A Wells with 519 Plasma Samples Assayed for t-Pa Antigen by the Present Invention

| $A_{492}$ | n |
|---|---|
| >150 | 3 |

"n" is the number of samples. The normal t-PA content is about 6 μg/l, which in this analysis method corresponds to a specific measurement result of about 200 milliabsorbance units (mA). Table I shows that, without using the present invention, the antigen content in about 2% of the samples will be overestimated by at least 25%. It should be recognized here that in clinical studies, serious measurement error in a few percent of the samples is sufficient to create considerable uncertainty and extra work.

It should be understood, of course, that the foregoing relates only to a preferred embodiment of the present invention and that numerous modifications or alterations may be made therein without departing from the spirit and the scope of the invention as set forth in the appended claims.

We claim:

1. A method of detecting an antigen in a sample comprising the steps of:
   a. coating a first solid phase and a second solid phase with an antigen-specific antibody;
   b. exposing the first solid phase to a solution containing:
      i. the antigen; and
      ii. between approximately 1 and 100 mg/l of antigen-specific antibody;
   c. exposing the second solid phase to a solution containing the antigen;
   d. determining the amount of antigen bound to the first solid phase and to the second solid phase; and
   e. quantifying the amount of antigen in the sample by subtracting the amount of antigen bound to the first solid phase from the amount of antigen bound to the second solid phase.

2. The method of claim 1, wherein in step (c) the solution further contains a non-antigen specific antibody.

3. The method of detecting an antigen of claim 2, wherein in step c, the second solid phase is first exposed to a solution containing the non-specific antibody and a solution containing the antigen is then added to the solution containing the non-specific antibody.

4. The method of detecting an antigen of claim 2, wherein the non-antigen-specific antibody and the antigen-specific antibody are derived from the same species.

5. The method of detecting an antigen of claim 1, wherein in step b, the first solid phase is first exposed to a solution containing the antigen-specific antibody and a solution containing the antigen is then added to the solution containing the antigen-specific antibody.

6. The method of detecting an antigen of claim 1, wherein the antibodies are selected from the group consisting of monoclonal antibodies and polyclonal antibodies.

7. The method of detecting an antigen of claim 1, wherein the first solid phase is the inner surface of a first test tube and the second solid phase is the inner surface of a second test tube.

8. The method of detecting an antigen of claim 1, wherein the first solid phase is the inner surface of a first well in a microtiter plate and the second solid phase is the inner surface of a second well in a microtiter plate.

9. The method of detecting an antigen of claim 1, wherein the solid phases are the surface of particles.

10. The method of detecting an antigen of claim 9, wherein the particles comprise material selected from the group consisting of agarose, polystyrene, latex, and polymethacrylate.

11. The method of detecting an antigen of claim 1, wherein the antibodies comprise γ-immunoglobulins.

12. The method of detecting an antigen of claim 1, wherein the antigen comprises tissue plasminogen activator antigen or urinary plasminogen activator.

13. The method of detecting an antigen of claim 1, wherein the method is a qualitative assay.

14. The method of claim 1, wherein the antigen-specific antibody in step (b) is between approximately 20 to 80 mg/l.

* * * * *